US012788631B2

(12) United States Patent
Hickey

(10) Patent No.: US 12,788,631 B2
(45) Date of Patent: Nov. 10, 2026

(54) IRRIGATION DAY CASSETTE

(71) Applicant: Johnson & Johnson Surgical Vision, Inc., Irvine, CA (US)

(72) Inventor: Lauren Hickey, Irvine, CA (US)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 254 days.

(21) Appl. No.: 16/256,996

(22) Filed: Jan. 24, 2019

(65) Prior Publication Data

US 2020/0237976 A1 Jul. 30, 2020

(51) Int. Cl.

*A61F 9/007* (2006.01)
*A61M 1/00* (2006.01)
*A61M 3/02* (2006.01)

(52) U.S. Cl.

CPC .......... *A61F 9/00745* (2013.01); *A61F 9/007* (2013.01); *A61M 1/72* (2021.05); *A61M 1/77* (2021.05); *A61M 3/0201* (2021.05); *A61M 1/804* (2021.05); *A61M 2205/12* (2013.01); *A61M 2210/0612* (2013.01)

(58) Field of Classification Search

CPC ............ A61M 1/0058; A61M 2205/12; A61M 2205/11; A61M 2205/128; A61M 2205/123; A61M 2205/121; A61M 39/24; A61M 3/0283; A61F 9/00736; A61F 9/007

See application file for complete search history.

(56) References Cited

U.S. PATENT DOCUMENTS

| | | | | |
|---|---|---|---|---|
| 4,735,610 | A * | 4/1988 | Akkas ................. | A61M 1/0062 604/319 |
| 5,676,530 | A * | 10/1997 | Nazarifar ............ | A61M 1/0058 417/477.2 |
| 5,810,766 | A * | 9/1998 | Barnitz ............... | A61M 1/0058 604/317 |
| 6,511,454 | B1 * | 1/2003 | Nakao ..................... | A61M 1/72 604/151 |
| 8,814,849 | B1 * | 8/2014 | Winsor ................. | A61M 39/24 604/536 |
| 9,775,964 | B2 * | 10/2017 | Eubanks ............. | A61M 3/0202 |
| 2005/0118048 | A1 * | 6/2005 | Traxinger ............. | A61M 39/08 417/477.2 |
| 2008/0300533 | A1 | 12/2008 | Lumpkin et al. | |
| 2009/0143746 | A1 * | 6/2009 | Mudd ................... | A61M 5/347 604/243 |
| 2013/0267779 | A1 * | 10/2013 | Woolford .............. | A61M 39/22 600/156 |
| 2015/0290387 | A1 | 10/2015 | Mollstam | |
| 2017/0304117 | A1 | 10/2017 | Gerg et al. | |

OTHER PUBLICATIONS

International Search Report and Written Opinion for Application No. PCTIB2020050238, mailed Mar. 24, 2020, 5 pages.

* cited by examiner

*Primary Examiner* — Courtney Fredrickson
*Assistant Examiner* — Anna E Vargas

(57) ABSTRACT

A phacoemulsification console including two cassettes within the system for use during cataract surgery. An irrigation cassette which is retained in the system for the duration of surgical procedures and an aspiration cassette which is replaced after each and every surgical procedure. The irrigation cassette is connected to the aspiration cassette via a valve having elastomeric properties.

17 Claims, 4 Drawing Sheets

IRRIGATION DAY CASSETTE

FIELD OF THE INVENTION

The present invention relates to phacoemulsification fluidics system control, and, more particularly a dual cassette receiving phacoemulsification console for irrigation and aspiration during cataract surgery.

BACKGROUND

Cataracts affect more than 22 million Americans age 40 and older. And as the U.S. population ages, more than 30 million Americans are expected to have cataracts by the year 2020. Cataract surgery entails the removal of a lens of an eye that has developed clouding of the eye's natural lens, or opacification. As a result of opacification, light is unable to travel to the retina, thereby causing vision loss. Once vision becomes impaired, cataract surgery is a viable option with a high level of success. During cataract surgery, a surgeon replaces the clouded lens with an intraocular lens (IOL).

Certain surgical procedures, such as phacoemulsification surgery, have been successfully employed in the treatment of certain ocular problems, such as cataracts. Phacoemulsification surgery utilizes a small corneal incision to insert the tip of at least one phacoemulsification handheld surgical implement, or handpiece, through the corneal incision. The handpiece includes a needle which is ultrasonically driven once placed within the incision to emulsify the eye lens, or to break the cataract into small pieces. The broken cataract pieces or emulsified eye lens may subsequently be removed using the same handpiece, or another handpiece, in a controlled manner. The surgeon may then insert a lens implant into the eye through the incision. The incision is allowed to heal, and the result for the patient is typically significantly improved eyesight.

During the phacoemulsification process for cataract removal, a single disposable plastic cassette is generally used to collect effluent material. This single cassette requires a prime on every insertion. The cost per case is a very sensitive factor for surgeons, which includes balanced salt solution ("BSS") usage and cassette cost. Currently a significant portion of BSS is used during prime to fill the line from the BSS bottle to the pack. Time and coordination is also required for a non-sterile nurse to spike and hang the BSS bottle after the sterile nurse has inserted the cassette. This can slow down the setup procedure as the sterile nurse may be waiting for this to occur to start prime. The irrigation side of the cassette has maintained sterility, but since it is physically part of the cassette, it is disposed of at the end of a case, in some cases along with the BSS bottle.

BRIEF SUMMARY OF THE INVENTION

The present invention provides for a surgical system, comprising a first cassette having at least one input; a second cassette having at least one input and at least one output; and a link between the first cassette and the second cassette; wherein the first cassette is used for multiple procedures and the second cassette is replaced after each procedure. The first cassette may be an irrigation cassette and the at least one input of the first cassette may be connected to a bottle or bag for irrigation. The second cassette is an aspiration cassette and may provide irrigation and aspiration to an eye. The present invention may also provide an inter-cassette irrigation connection.

BRIEF DESCRIPTION OF THE DRAWINGS

This disclosure is illustrated by way of example and not by way of limitation in the accompanying figure(s). The figure(s) may, alone or in combination, illustrate one or more embodiments of the disclosure. Elements illustrated in the figure(s) are not necessarily drawn to scale. Reference labels may be repeated among the figures to indicate corresponding or analogous elements.

The detailed description makes reference to the accompanying figures in which.

DETAILED DESCRIPTION

The figures and descriptions provided herein may have been simplified to illustrate aspects that are relevant for a clear understanding of the herein described apparatuses, systems, and methods, while eliminating, for the purpose of clarity, other aspects that may be found in typical similar devices, systems, and methods. Those of ordinary skill may thus recognize that other elements and/or operations may be desirable and/or necessary to implement the devices, systems, and methods described herein. But because such elements and operations are known in the art, and because they do not facilitate a better understanding of the present disclosure, for the sake of brevity a discussion of such elements and operations may not be provided herein. However, the present disclosure is deemed to nevertheless include all such elements, variations, and modifications to the described aspects that would be known to those of ordinary skill in the art.

Embodiments are provided throughout so that this disclosure is sufficiently thorough and fully conveys the scope of the disclosed embodiments to those who are skilled in the art. Numerous specific details are set forth, such as examples of specific components, devices, and methods, to provide a thorough understanding of embodiments of the present disclosure. Nevertheless, it will be apparent to those skilled in the art that certain specific disclosed details need not be employed, and that exemplary embodiments may be embodied in different forms. As such, the exemplary embodiments should not be construed to limit the scope of the disclosure. As referenced above, in some exemplary embodiments, well-known processes, well-known device structures, and well-known technologies may not be described in detail.

The disclosed allows for the irrigation functionality of a phacoemulsification system to be decoupled from the aspiration, thus allowing for extended use of an irrigation cassette across multiple patients, minimizing cost per case, as well as setup time for the surgical center.

Figure 1:
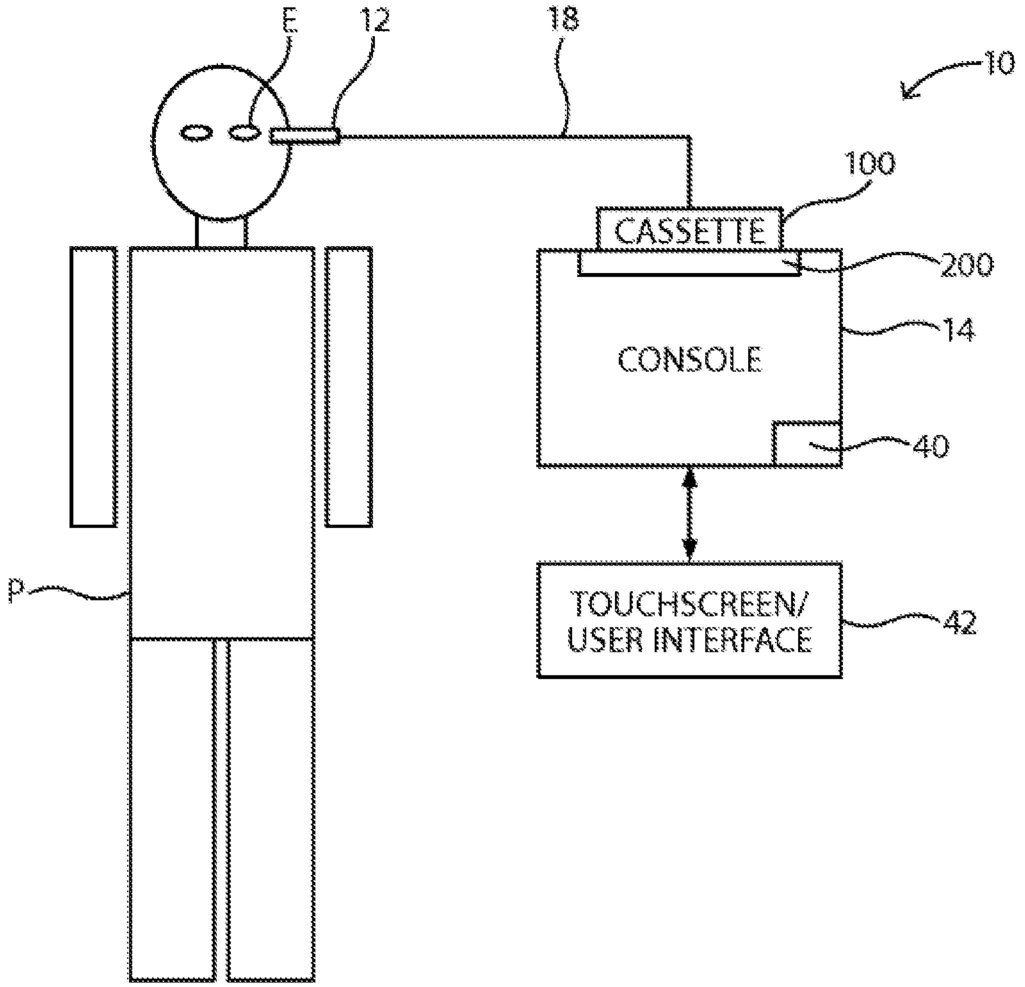
FIG. 1 schematically illustrates an eye treatment system in which a cassette couples an eye treatment probe with an eye treatment console.

Referring to FIG. 1, a system 10 for treating an eye E of a patient P generally includes an eye treatment probe handpiece 12 coupled to a console 14 by a cassette 100 mounted on the console via interface 200. Handpiece 12 may include a handle for manually manipulating and supporting an insertable probe tip. The probe tip has a distal end which is insertable into the eye, with one or more lumens in the probe tip allowing irrigation fluid to flow from the console 14 and/or cassette 100 into the eye. Aspiration fluid may also be withdrawn through a lumen of the probe tip, with the console 14 and cassette 100 generally including a vacuum aspiration source, a positive displacement aspiration pump, or both to help withdraw and control a flow of surgical fluids into and out of eye E. As the surgical fluids may include biological materials that should not be transferred between patients, cassette 100 will often be disposable or comprise a disposable (or alternatively, re-sterilizable) structure, with the surgical fluids being transmitted through conduits of the cassette that avoid direct contact in between those fluids and the components of console 14.

When a distal end of the probe tip of handpiece 12 is inserted into an eye E, for example, for removal of a lens of a patient with cataracts, an electrical conductor and/or pneumatic line (not shown) may supply energy from console 14 to an ultrasound transmitter of the handpiece, a cutter mechanism, or the like. Alternatively, the handpiece 12 may be configured as an irrigation/aspiration (FA) or vitrectomy handpiece. Also, the ultrasonic transmitter may be replaced by other means for emulsifying a lens, such as a high energy laser beam. The ultrasound energy from handpiece 12 helps to fragment the tissue of the lens, which can then be drawn into a port of the tip by aspiration flow. So as to balance the volume of material removed by the aspiration flow, an irrigation flow through handpiece 12 (or a separate probe structure) may also be provided, with both the aspiration and irrigations flows being controlled by console 14.

So as to avoid cross-contamination between patients and/or to avoid incurring excessive expenditures for each procedure, cassette 100 and its conduit(s) 18 may be disposable. Alternatively, the conduit(s) or tubing line(s) may be disposable, with the cassette body and/or other structures of the cassette being sterilizable. Regardless, the disposable components of the cassette are typically configured for use with a single patient and may not be suitable for sterilization. The cassette will interface with reusable (and often quite expensive) components of console 14, which may include one or more peristaltic pump rollers, a Venturi or other vacuum source, a controller 40, and the like.

Controller 40 may include an embedded microcontroller and/or many of the components common to a personal computer, such as a processor, data bus, a memory, input and/or output devices (including a touch screen user interface 42), and the like. Controller 40 will often include both hardware and software, with the software typically comprising machine readable code or programming instructions for implementing one, some, or all of the methods described herein. The code may be embodied by a tangible media such as a memory, a magnetic recording media, an optical recording media, or the like. Controller 40 may have (or be coupled to) a recording media reader, or the code may be transmitted to controller 40 by a network connection such as an internet, an intranet, an Ethernet, a wireless network, or the like. Along with programming code, controller 40 may include stored data for implementing the methods described herein, and may generate and/or store data that records parameters corresponding to the treatment of one or more patients. Many components of console 14 may be found in or modified from known commercial phacoemulsification.

Figure 2A:
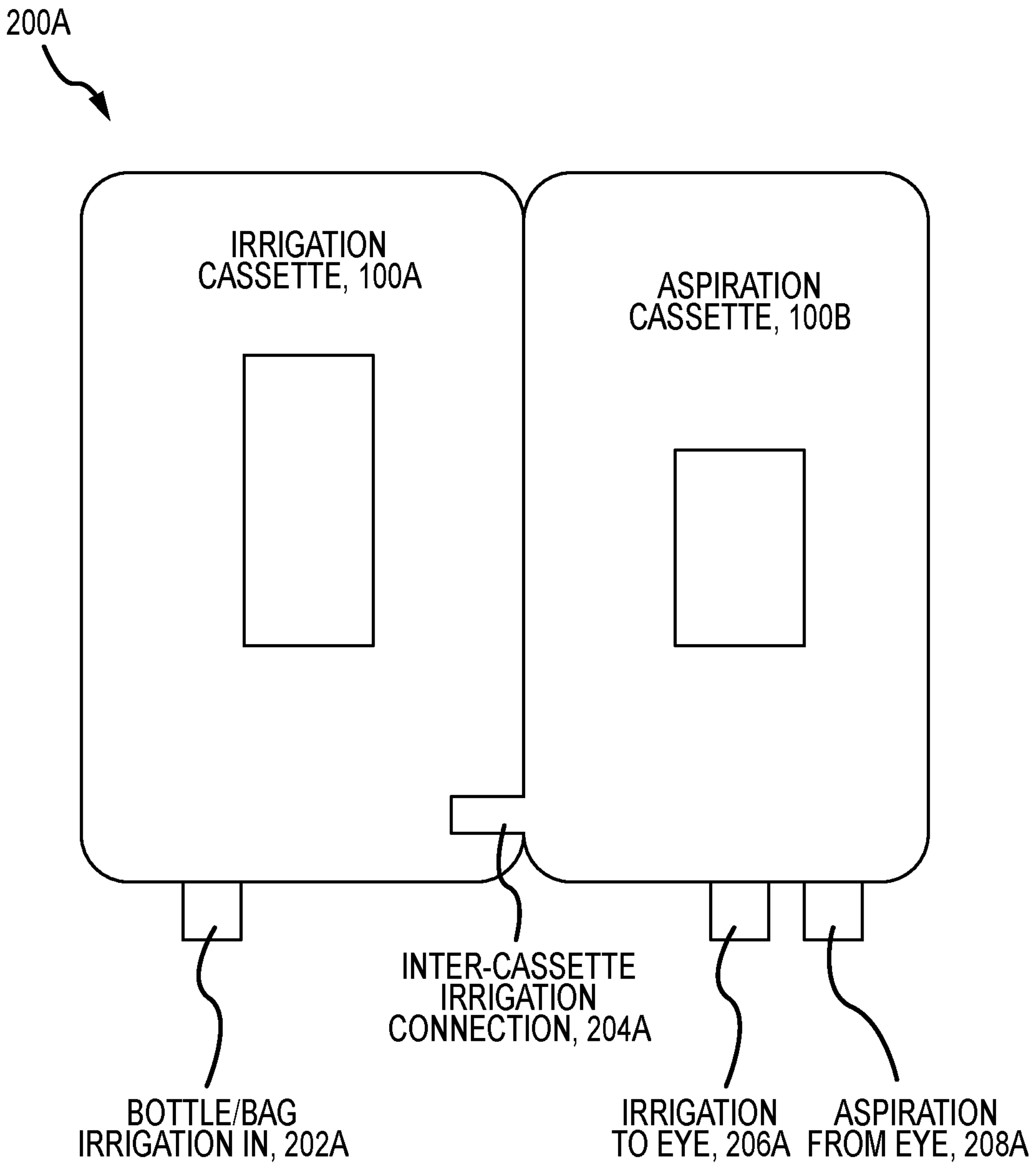
FIG. 2A illustrates an irrigation cassette 100A and aspiration cassette 100B in accordance with an exemplary embodiment of the disclosed invention.
Figure 2B:
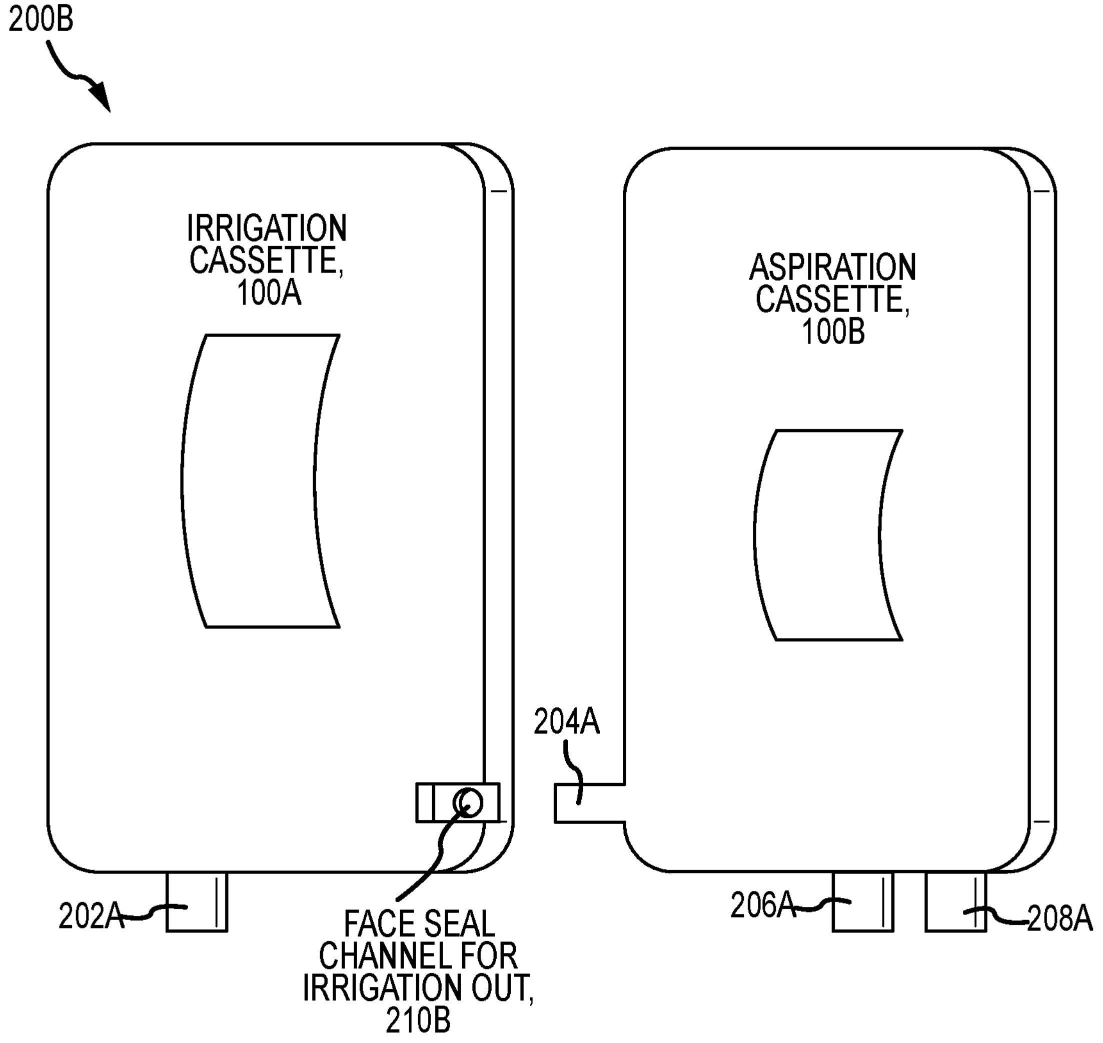
FIG. 2B illustrates an irrigation cassette 100A and aspiration cassette 100B in accordance with another exemplary embodiment of the disclosed invention.

FIG. 2A illustrates, in diagram 200A, console 14 (shown in FIG. 1) receiving more than one cassette. Interface 200 (shown in FIG. 1) may be configured to receive multiple cassettes via two pack capture interfaces. In the illustrated example, cassette 100 may include an irrigation cassette 100A and an aspiration cassette 100B. The cassettes may be replaced at different intervals. For example, irrigation cassette 100A may be retained in the system for the duration of cases in one day, while aspiration cassette 100B may be replaced more frequently, such as after every use. A BSS source may be connected via a traditional spike 202A to irrigation cassette 100A. Aspiration cassette 100B may connect to irrigation cassette 100A via a check valve 204A. Aspiration cassette 100B may include irrigation out 206A and one or more aspiration tubing lines 208A. Tubing lines out 208A may connect to one or more system handpieces 12 via line 18 as shown in FIG. 1. FIG. 2B illustrates diagram 200B showing irrigation cassette 100A and aspiration cassette 100B in a disconnected state. As shown, valve 204A, e.g. a check valve, connects to face seal channel 210B for irrigation out. In at least one embodiment, aspiration cassette 100B may make the connection to irrigation cassette 100A automatically during the aspiration cassette capture.

Figure 3:
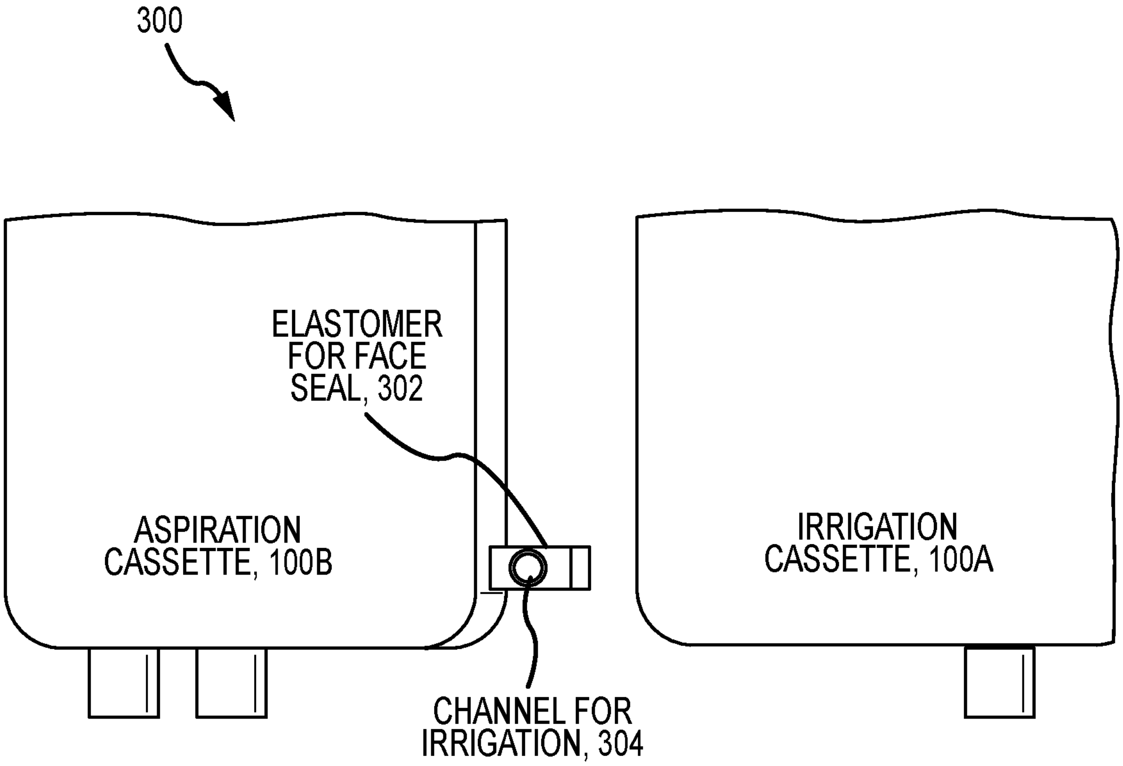
FIG. 3 illustrates an irrigation cassette 100A and aspiration cassette 100B in accordance with yet another exemplary embodiment of the disclosed invention.

FIG. 3 illustrates diagram 300 showing a rear view of irrigation cassette 100A and aspiration cassette 100B in an alternative embodiment. Aspiration cassette 100B may have a channel for irrigation 304 including an elastomer for face seal 302.

Irrigation cassette 100A may or may not have pressurized infusion. Within irrigation cassette 100A, valve 204A guarantees sterility of the irrigation cassette. Valve fluid that has touched the eye should not contact the irrigation in fluid. In at least one embodiment, a full prime of irrigation in, irrigation out, and aspiration would only need to occur at insertion of the irrigation cassette 100A and aspiration cassette 100B, which would typically occur at the beginning of the day. At the conclusion of a case, used aspiration cassette 100B may be discarded and replaced by a new aspiration cassette. At this point, a full prime would not be required. Instead, only an aspiration cassette prime, including irrigation out and aspiration, would need to be performed. As a result, this reduces the volume used during the case prime by 55% based on tubing diameters, such as OP071 tubing diameters.

The disclosed system provides invaluable and crucial cost and time benefits. For example, the cost of an irrigation cassette may be amortized over the surgical procedures scheduled for the day. Further, time is saved on priming the phacoemulsification system and time and money is saved on BSS usage as the BSS is used more efficiently.

Those of skill in the art will appreciate that the herein described apparatuses, engines, devices, systems and methods are susceptible to various modifications and alternative constructions. There is no intention to limit the scope of the invention to the specific constructions described herein. Rather, the herein described systems and methods are intended to cover all modifications, alternative constructions, and equivalents falling within the scope and spirit of the disclosure, any appended claims and any equivalents thereto.

In the foregoing detailed description, it may be that various features are grouped together in individual embodiments for the purpose of brevity in the disclosure. This method of disclosure is not to be interpreted as reflecting an intention that any subsequently claimed embodiments require more features than are expressly recited.

Further, the descriptions of the disclosure are provided to enable any person skilled in the art to make or use the disclosed embodiments. Various modifications to the disclosure will be readily apparent to those skilled in the art, and the generic principles defined herein may be applied to other variations without departing from the spirit or scope of the disclosure. Thus, the disclosure is not intended to be limited to the examples and designs described herein, but rather is to be accorded the widest scope consistent with the principles and novel features disclosed herein.

The invention claimed is:

1. A system, comprising:

an aspiration cassette adapted to be attached to a multi-cassette receiving interface of a surgical console, the aspiration cassette configured to provide both aspiration and irrigation with at least one input and at least one output;

an irrigation cassette adapted to be attached to the multi-cassette receiving interface, the irrigation cassette configured to provide only irrigation to the aspiration cassette, the irrigation cassette including at least one input for coupling to an irrigation source; and a one-way fluid link between the irrigation cassette and the aspiration cassette to provide irrigation to the aspiration cassette, the one-way fluid link providing the only fluid link between the irrigation cassette and the aspiration cassette;

wherein the irrigation cassette is configured to be used for multiple procedures and the aspiration cassette is configured to be replaced after each procedure; and wherein the aspiration cassette includes at least one valve having a face seal and the irrigation cassette includes a face seal channel to receive the face seal of the aspiration cassette to form the one-way fluid link between the irrigation cassette and the aspiration cassette, wherein the face seal is configured to automatically connect to the face seal channel of the irrigation cassette during cassette capture.

2. The system of claim 1, wherein the at least one input of the irrigation cassette is connected to a bottle or bag for irrigation.

3. The system of claim 1, wherein the at least one output of the aspiration cassette is an eye irrigation output.

4. The system of claim 1, wherein the at least one input of the aspiration cassette is an eye aspiration input.

5. The system of claim 1, wherein the one-way fluid link is an inter-cassette irrigation connection.

6. The system of claim 5, wherein the face seal of the aspiration cassette is comprised of an elastomer.

7. The system of claim 5, wherein the one-way fluid link comprises a channel for irrigation.

8. A phacoemulsification system, comprising:

a surgical handpiece;

a surgical console configured to receive multiple cassettes via a two pack capture interface;

an irrigation cassette adapted to be removably coupled to the two pack capture interface of the surgical console; and an aspiration cassette adapted to be removably coupled to the two pack capture interface of the surgical console;

wherein the aspiration cassette is connected to the surgical handpiece via one or more tubing lines to provide both aspiration and irrigation;

wherein the irrigation cassette is configured to provide only irrigation to the aspiration cassette via a one-way fluid link, the one-way fluid link providing the only fluid link between the irrigation cassette and the aspiration cassette;

wherein the irrigation cassette is configured to be used for multiple procedures and the aspiration cassette is configured to be replaced after each procedure; and wherein the aspiration cassette includes at least one valve having a face seal and the irrigation cassette includes a face seal channel for receiving the face seal of the aspiration cassette to provide the one-way fluid link, the face seal configured to automatically connect to the face seal channel of the irrigation cassette during cassette capture.

9. The system of claim 8, wherein the face seal has elastomeric properties.

10. The system of claim 8, wherein the irrigation cassette is configured to be utilized for more than one surgical procedure.

11. The system of claim 8, wherein the aspiration cassette is configured to be replaced after each surgical procedure.

12. The system of claim 8, wherein the aspiration cassette and irrigation cassette are configured to be replaced at differing intervals.

13. The system of claim 8, wherein the at least one valve is a check valve.

14. The system of claim 13, wherein the face seal has elastomeric properties.

15. A system, comprising:

an irrigation cassette adapted to be attached to a multi-cassette receiving interface of a surgical console, the irrigation cassette having at least one input for coupling to an irrigation source; and an aspiration cassette adapted to be attached to the multi-cassette receiving interface, the aspiration cassette having at least one input and at least one output to respectively provide aspiration and irrigation to a patient;

wherein the irrigation cassette is configured to provide only irrigation to the aspiration cassette via a one-way fluid link, the one-way fluid link providing the only fluid link between the irrigation cassette and the aspiration cassette;

wherein the aspiration cassette includes at least one valve having a face seal and the irrigation cassette includes a face seal channel to receive the face seal of the aspiration cassette, wherein the face seal is configured to automatically connect to the face seal channel of the irrigation cassette during aspiration cassette capture to establish the one-way fluid link between the irrigation cassette and the aspiration cassette; and wherein the irrigation cassette is configured for use in multiple procedures and the aspiration cassette is configured to be replaced after each procedure.

16. The system of claim 15, wherein the at least one valve comprises a check valve.

17. The system of claim 15, wherein the irrigation cassette includes pressurized infusion.

* * * * *